(12) United States Patent
Tatkov

(10) Patent No.: US 9,539,401 B2
(45) Date of Patent: Jan. 10, 2017

(54) TRACHEAL COUPLINGS AND ASSOCIATED SYSTEMS AND METHODS

(75) Inventor: Stanislav Tatkov, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 554 days.

(21) Appl. No.: 13/637,634

(22) PCT Filed: Mar. 29, 2011

(86) PCT No.: PCT/NZ2011/000040
§ 371 (c)(1),
(2), (4) Date: Dec. 17, 2012

(87) PCT Pub. No.: WO2011/122964
PCT Pub. Date: Oct. 6, 2011

(65) Prior Publication Data
US 2013/0081616 A1    Apr. 4, 2013

Related U.S. Application Data

(60) Provisional application No. 61/318,542, filed on Mar. 29, 2010.

(51) Int. Cl.
*A61M 16/04* (2006.01)
*A61M 16/00* (2006.01)
(Continued)

(52) U.S. Cl.
CPC ......... *A61M 16/04* (2013.01); *A61M 16/0057* (2013.01); *A61M 16/0465* (2013.01);
(Continued)

(58) Field of Classification Search
CPC .............. A61M 16/04; A61M 16/0465; A61M 16/0875; A61M 16/208; A61M 39/10; A61M 2206/10; A61M 2206/20; A62B 9/04
(Continued)

(56) References Cited

U.S. PATENT DOCUMENTS 2,031,849 A * 2/1936 O'Leary ................. F16L 39/00
138/44
3,948,274 A 4/1976 Zeldman et al.
(Continued)

FOREIGN PATENT DOCUMENTS

GB       2069849 A  *  9/1981  ............ A61M 16/00
WO    WO 01-66175 A1    9/2001

*Primary Examiner* — Lynne Anderson
*Assistant Examiner* — Joseph D Boecker
(74) *Attorney, Agent, or Firm* — Knobbe Martens Olson & Bear LLP

(57) ABSTRACT

A tracheal coupling for interfacing between a patient and a gases source, the connector comprising a patient port (33) for connecting to the trachea interface/insert, an outlet port (36), and inlet port (31) between patient port and outlet port for receiving a flow of gases from the gases flow source, the connector restricting expiratory flow in use to produce PEEP of at least 1 cm H2O when flow to the inlet port is 50 liters per minute. A system or method for supplying gases to a patient using the connector is also disclosed. Flow restriction is implemented using an orifice that can be adjustable, jetting or turbulence induced by a directed flow nozzle (30). PEEP can also be varied by flow control of gas source.

19 Claims, 9 Drawing Sheets

(51) Int. Cl.
  *A61M 16/10* (2006.01)
  *A61M 16/20* (2006.01)
  *A61M 16/08* (2006.01)

(52) U.S. Cl.
  CPC .... *A61M 16/0816* (2013.01); *A61M 16/0833* (2014.02); *A61M 16/0866* (2014.02); *A61M 16/1045* (2013.01); *A61M 16/208* (2013.01); *A61M 16/0488* (2013.01); *A61M 16/20* (2013.01)

(58) Field of Classification Search
  USPC .......... 128/204.18, 204.24, 204.25, 207.14, 128/207.16; 285/132.1; 604/26, 284, 285; 606/108
  See application file for complete search history.

(56) References Cited

U.S. PATENT DOCUMENTS

| | | | | |
|---|---|---|---|---|
| 3,993,059 A * | 11/1976 | Sjostrand | ............ | A61M 16/00 128/205.13 |
| 4,274,406 A | 6/1981 | Bartholomew | | |
| 4,315,505 A | 2/1982 | Crandall et al. | | |
| 4,520,812 A | 6/1985 | Freitag et al. | | |
| 4,655,213 A * | 4/1987 | Rapoport | ............... | A61M 16/06 128/205.25 |
| 4,870,963 A * | 10/1989 | Carter | ................. | A61M 16/208 128/205.24 |
| 5,140,982 A * | 8/1992 | Bauman | ........... | A61M 16/0084 128/205.11 |
| 5,271,388 A * | 12/1993 | Whitwam | ........... | A61M 16/00 128/204.18 |
| 5,590,644 A | 1/1997 | Rosenkoetter | | |
| 5,957,134 A * | 9/1999 | Lee | ....................... | A61M 16/04 128/207.14 |
| 6,102,038 A * | 8/2000 | DeVries | .............. | A61M 16/208 128/204.23 |
| 7,341,059 B2 * | 3/2008 | Moody | ................. | A61M 16/00 128/204.18 |
| 2009/0139530 A1 | 6/2009 | Landis et al. | | |
| 2010/0071693 A1 * | 3/2010 | Allum | .................... | A61M 16/04 128/203.27 |
| 2010/0089399 A1 * | 4/2010 | Landis | ............. | A61M 16/0463 128/205.12 |
| 2010/0095965 A1 * | 4/2010 | Piper | ................. | A61M 16/0816 128/205.24 |
| 2012/0048274 A1 * | 3/2012 | Bayron | ............. | A61M 16/0463 128/205.14 |

* cited by examiner

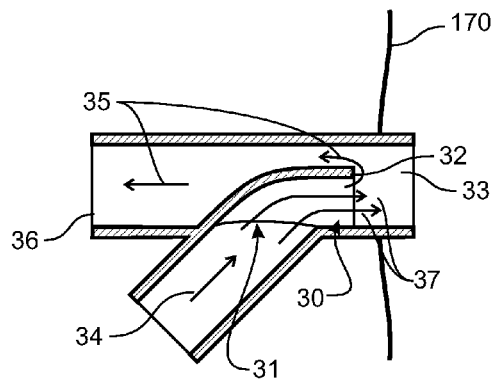
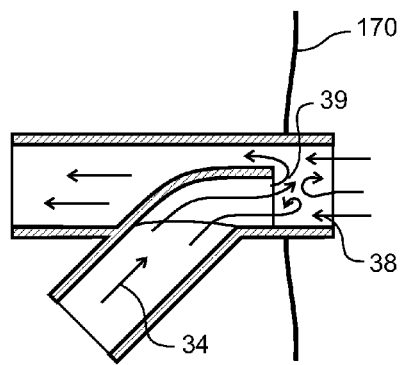
FIGURE 18  FIGURE 19
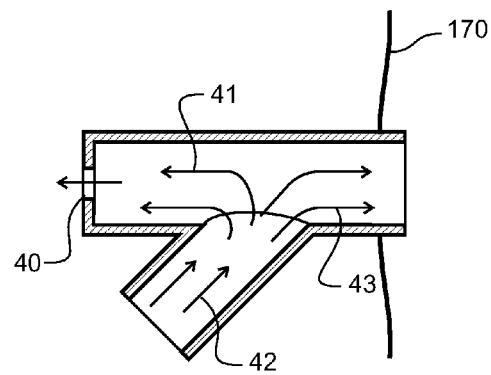
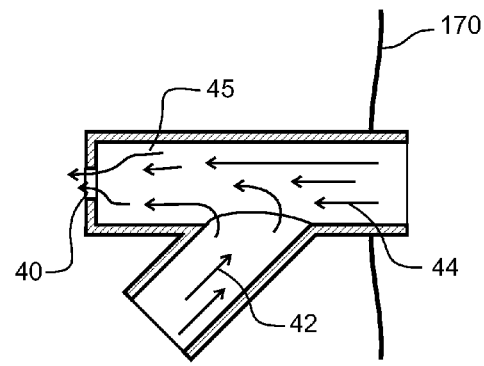
FIGURE 20  FIGURE 21
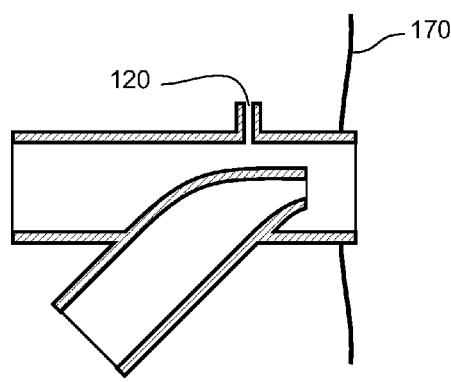
FIGURE 22

TRACHEAL COUPLINGS AND ASSOCIATED SYSTEMS AND METHODS

FIELD OF INVENTION

The present invention relates to tracheal couplings (e.g. connectors/interfaces) for connecting/interfacing between an intubated or tracheotomised spontaneously breathing patient and a gas supply conduit from a continuous breathing gas supply.

SUMMARY OF THE INVENTION

An object of the invention is to provide a tracheal coupling which will at least go some way towards providing a useful choice.

In one aspect the present invention may be said to consist in a tracheal coupling for interfacing between a patient and a gases source, the connector comprising a patient port for connecting to the trachea interface/insert, an outlet port, and inlet port between patient port and outlet port for receiving a flow of gases from the gases flow source, the connector restricting expiratory flow in use to produce PEEP of at least 1 cm $H_2O$ when flow to the inlet port is 50 liters per minute.

Preferably the coupling is a connector that can be connected to a trachea interface/insert in or on a patient to interface between a patient and a gases source.

Preferably the trachea interface/insert is one or more of: a trachea button, a endotracheal tube, a tacheostomy tube, a laryngeal mask.

Alternatively the coupling comprises a trachea interface that can be attached to a patient to interface between a patient and a gases source.

Preferably the flow restriction includes a restriction between inlet port and outlet port or at outlet port.

Preferably the flow restriction includes an adjustable orifice.

Preferably the flow restriction is caused by turbulence from inlet flow.

Preferably the flow restriction is caused by jetting air from inlet flow.

Preferably the connector includes a nozzle extending from the inlet port toward the patient port.

Preferably the nozzle extends through the patient port.

Preferably the nozzle includes a bend in a portion between an outlet end of the nozzle and the patient port.

Preferably the coupling further comprises a pressure relief valve.

Preferably the restriction comprises a heat and moisture exchanger.

In another aspect the present invention may be said to consist in a system for supplying breathing gases to a patient comprising an airflow source including an adjustable flow control, and a tracheal coupling for receiving gases from the airflow source in excess for a patient's breathing requirements, supplying breathing gases for the patient to inhale, and releasing exhaled gases and uninhaled gases through an outlet port, the connector restricting expiratory flow to generate amount of PEEP according to flow through connector, and thereby according to the setting of the adjustable flow control of the airflow source.

Preferably the tracheal coupling is a connector that can be connected to a trachea interface/insert in or on a patient.

Preferably the trachea interface/insert is one of: a trachea button, a endotracheal tube, a tacheostomy tube, a laryngeal mask.

Preferably the coupling comprises a trachea interface that can be attached to a patient to interface between a patient and a gases source.

Preferably the flow restriction includes a restriction between an inlet port and outlet port, or at the outlet port.

Preferably the flow restriction includes an adjustable orifice.

Preferably the system further comprises a pressure relief valve.

Preferably the flow restriction is caused by turbulence from inlet flow.

Preferably the flow restriction is caused by jetting air from inlet flow.

Preferably the connector includes a nozzle extending from the inlet port toward the patient port.

Preferably the nozzle extends through the patient port.

Preferably the nozzle includes a bend in a portion between an outlet end of the nozzle and the patient port.

In another aspect the present invention may be said to consist in a tracheal coupling comprising a patient port, an outlet port, an inlet port between the patient port and the outlet port, such that flow from the inlet port can go to the patient port or direct to the outlet port, and a flow restriction between the inlet port and the outlet port, or at the outlet port.

Preferably the flow restriction includes an adjustable orifice.

Preferably the tracheal coupling further comprises a pressure relief valve.

In another aspect the present invention may be said to consist in a tracheal coupling comprising a patient port, an outlet port, an inlet port between the patient port and the outlet port, such that flow from inlet port can go to the patient port or direct to outlet port, and a jet or nozzle discharging flow from the inlet port toward the patient port in the flow path of gases flowing from the patient port to the outlet port.

Preferably the tracheal coupling further comprises a restriction between the inlet port and the outlet port, or at the outlet port.

Preferably the flow restriction includes an adjustable orifice.

Preferably the tracheal coupling further comprises a pressure relief valve.

In another aspect the present invention may be said to consist in a method of providing breathing gases to a patient comprising: a) attaching a tracheal coupling to a breathing tube of the patient, the coupling having a patient port, an outlet port, an inlet port between the patient port and the outlet port, such that flow from inlet port can go to the patient port or direct to the outlet port, and a jet or nozzle discharging flow from the inlet port toward the patient port in the flow path of gases flowing from the patient port to the outlet port, b) selecting a flow level for a supply of gases to the connector to generate a desired amount of PEEP, c) supplying the flow level of gases to the inlet port of the connector.

In another aspect the present invention may be said to consist in a method of providing breathing gases to a patient comprising: a) attaching a tracheal coupling to a breathing tube of the patient, the connector having a patient port, an outlet port, an inlet port between the patient port and the outlet port, such that flow from inlet port can go to the patient port or direct to outlet port, and a jet or nozzle discharging flow from the inlet port toward the patient port in the flow path of gases flowing from the patient port to the outlet port, b) adjusting a flow restriction for the connector according to an expected flow of gases and a desired amount of PEEP c) supplying a flow of gases to the inlet port of the connector.

In another aspect the present invention may be said to consist in a connector for interfacing between an endotracheal tube or tracheostomy tube and a gases source, the connector comprising a patient port for connecting to the endotracheal or tracheostomy tube, an outlet port, and inlet port between patient port and outlet port for receiving a flow of gases from the gases flow source, the connector restricting expiratory flow in use to produce PEEP of at least 1 cm $H_2O$ when flow to the inlet port is 50 liters per minute.

In another aspect the present invention may be said to consist in a system for supplying breathing gases to a patient fitted with an endotracheal or tracheostomy tube comprising an airflow source including an adjustable flow control, and a connector receiving gases from the airflow source in excess for a patient's breathing requirements, supplying breathing gases for the patient to inhale, and releasing exhaled gases and uninhaled gases through an outlet port, the connector restricting expiratory flow to generate amount of PEEP according to flow through connector, and thereby according to the setting of the adjustable flow control of the airflow source.

In another aspect the present invention may be said to consist in a tracheal connector comprising a patient port, an outlet port, an inlet port between the patient port and the outlet port, such that flow from the inlet port can go to the patient port or direct to the outlet port, and a flow restriction between the inlet port and the outlet port, or at the outlet port.

In another aspect the present invention may be said to consist in a tracheal connector comprising a patient port, an outlet port, an inlet port between the patient port and the outlet port, such that flow from inlet port can go to the patient port or direct to outlet port, and a jet or nozzle discharging flow from the inlet port toward the patient port in the flow path of gases flowing from the patient port to the outlet port.

As used in this specification, "trachea connector" means a connector coupling between a gases supply conduit and the open end of a tracheostomy tube or ET tube.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The term "comprising" is used in the specification and claims, means "consisting at least in part of". When interpreting a statement in this specification and claims that includes "comprising", features other than that or those prefaced by the term may also be present. Related terms such as "comprise" and "comprises" are to be interpreted in the same manner.

BRIEF DESCRIPTION OF THE DRAWINGS

Embodiments of the present invention will be described with reference to the accompanying drawings.

FIG. 2A illustrates the flow through the connector during patient inhalation.

FIG. 2B illustrates the flow through the connector during patient exhalation.

FIG. 3A illustrates flows through the connector during patient inhalation.

FIG. 3B illustrates flows through the connector during patient exhalation.

FIG. 4A illustrates flows through the connector during patient inhalation.

FIG. 4B illustrates flows through the connector during patient exhalation.

FIGS. 18 to 28 show various aspects of a trachea interface with a body and mask with PEEP control.

DETAILED DESCRIPTION

Figure 1:
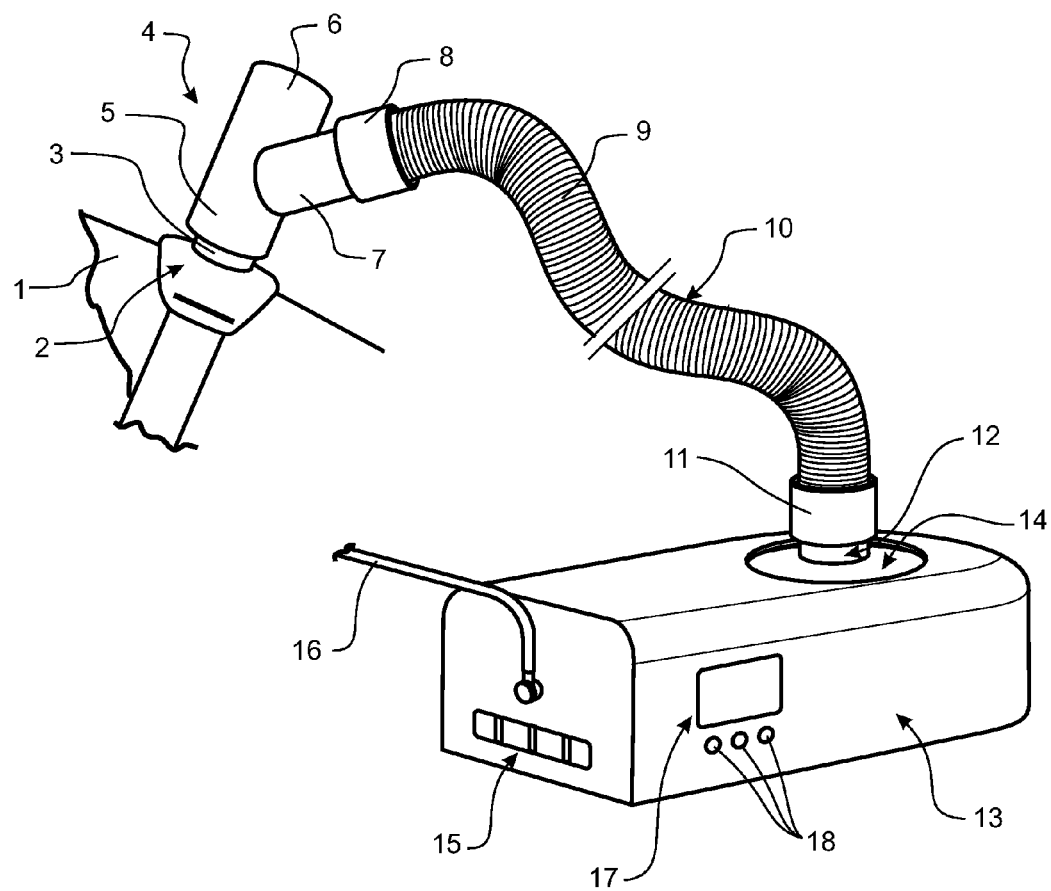
FIG. 1 illustrates a system for supplying breathing gases to a tracheotomised patient.

Tracheal couplings (e.g. in the form of connectors of trachea interfaces) according to the present invention are intended to be used in conjunction with the breathing gases supply system as generally depicted in FIG. 1. A tracheal coupling provides for passage of breathing gases (e.g. oxygen)/interfacing between a high flow gases supply and a patient (such as a tracheotomised or intubated patient.) A tracheal coupling can take the form of a connector that couples to a trachea insert/interface in or on a tracheotomised or intubated patient, either nasally or orally or otherwise. Alternatively, it can take the form of a trachea interface which can be attached to a tracheotomised/intubated patient. The tracheal coupling can be used with other high flow gases sources, such as a supply of air from a wall outlet or ventilator. The tracheal couplings are intended for use in a high flow therapy situation (e.g., the gas supply exceeds peak inspiratory flow) where the patient is spontaneously breathing. This means that a substantial proportion of the air supplied to the connector vents directly to the room without being breathed by the patient.

FIG. 1 illustrates a system into which tracheal couplings in the form of connectors according to the present invention may be incorporated. An external portion to a tracheostomy tube extends out of the neck of patient 1. A male connector 3 extends from the tracheostomy tube. A trachea connector 4 includes a patient end 5 connected to the male connector 3 of the tracheostomy tube. The connector 4 includes outlet end 6 and an inlet tube 7. The inlet tube is connected to the cuff 8 of a breathing tube 10. The breathing tube includes a flexible conduit 9 for supplying breathing gases to the patient. A cuff 11 at the other end of the breathing tube 10 is connected to outlet connector 12 of a gases flow source. The gases flow source may be a flow generator 13. The flow generator 13 may include a humidification system including humidification chamber 14. Breathing gases can be delivered to the user at, or near, optimal temperature and humidity (37° C., 44 mg/L humidity) as the gases are delivered. Emulating the conditions within healthy adult lungs (37° C., 44 mg/L humidity) can help maintain healthy mucociliary function in users with respiratory disorders affecting secretion.

The flow generator 13 typically includes a blower receiving air from an air intake 15 and optionally oxygen from oxygen supply line 16. A user interface may include a display screen 17 and user controls 18. The user controls may be in the form of buttons on the housing of the flow generator or combined with the display screen as a touch screen on the flow generator. An example flow generator for use in this application is the Fisher & Paykel Healthcare AIRVO™. The flow generator includes a flow sensor and a feedback control which monitors the delivered flow and varies the blower speed to maintain the output flow of the generator at a level set through the user controls.

The trachea connector 4 may also be used with the endotracheal tube (ET tube) of orally or nasally intubated patients. Endotracheal tubes and tracheostomy tubes are trachea inserts/interfaces. Other types of trachea inserts/interfaces that a trachea connector can be used with or connected to comprise stoma (trachea) buttons, and laryngeal masks.

Tracheal couplings in the form of trachea interfaces could also be used with the blower 17 and conduit 10 system shown in FIG. 1.

Figure 2A:
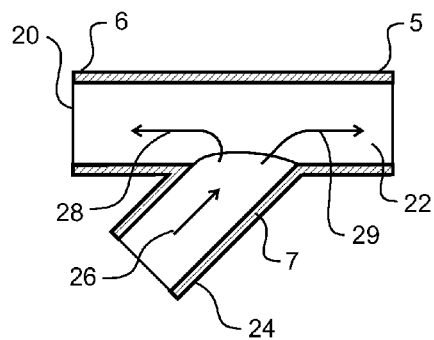
FIGS. 2A and 2B illustrate a prior art trachea connector.
Figure 2B:
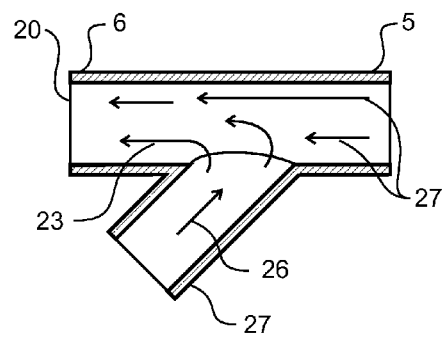

A prior art trachea coupling in the form of a connector is illustrated in FIGS. 2A and 2B. The connector includes an inner surface 22 at end 5 for connecting over the outlet 3 of the tracheostomy tube, an outer surface 24 of inlet tube 7 for fitting inside the cuff 8 of the breathing tube and an open outlet at end 6. The connector is for use in a high flow therapy where the patient is spontaneously breathing. The connector is not for use in a controlled mechanical ventilation. The connector is illustrated in FIG. 2A with typical flows during patient inhalation and in FIG. 2B with typical flows during patient exhalation. During patient inhalation, a portion 28 of inlet flow 26 flows directly to outlet 20 of the connector. Another portion 29 of inlet flow 26 flows to the patient through end 5. During exhalation, a flow 26 continues to enter the connector from the flow generator and, as indicated by arrows 23 flows to the outlet 20 together with flow 27 being returned through port 5 from the patient.

Figure 11:
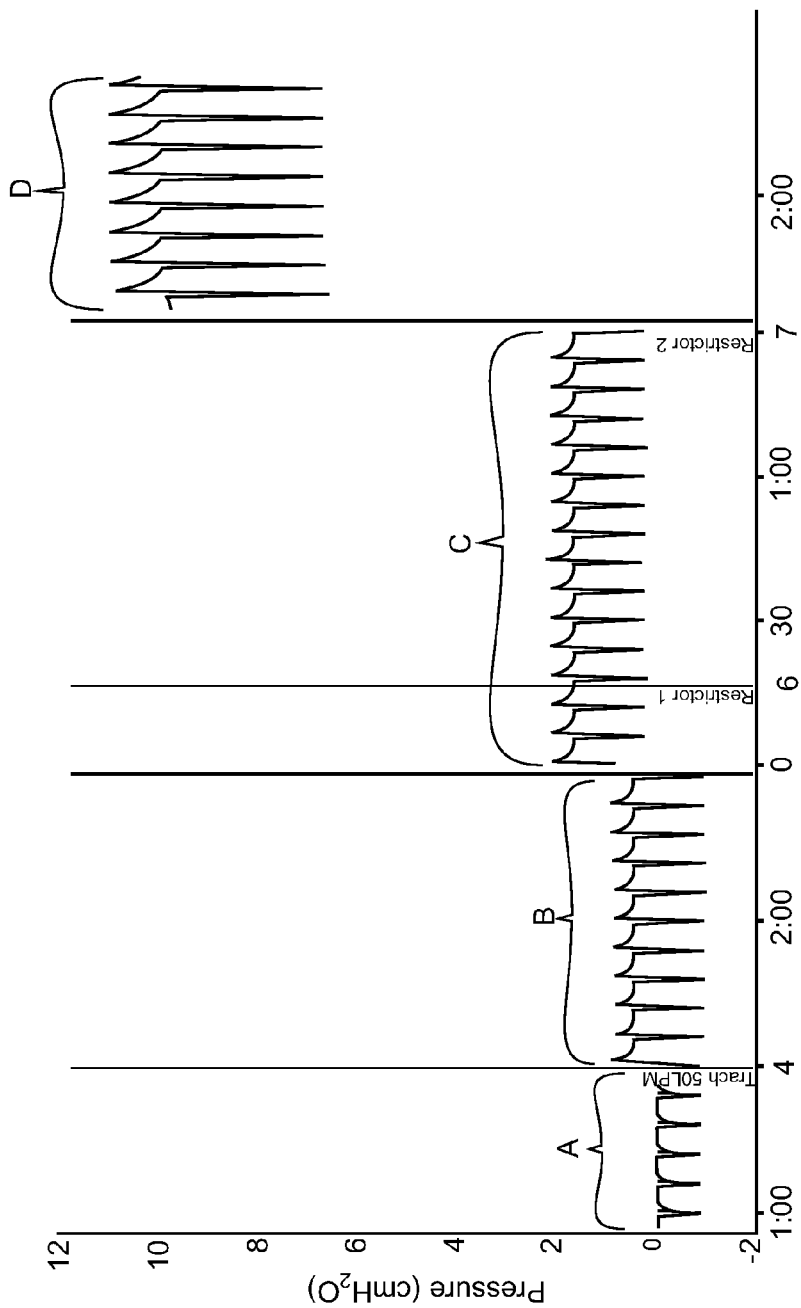
FIG. 11 is a plot of pressure versus time illustrating the pressure generated at the internal end of the tracheostomy by three different tracheal connectors under high flow supply conditions (50 liters per minute) used in conjunction with a lung simulator. Pressure generated at the end of the tracheostomy tube in the patient airway of the prior art tracheal connector with no supply flow is also shown.
Figure 13:
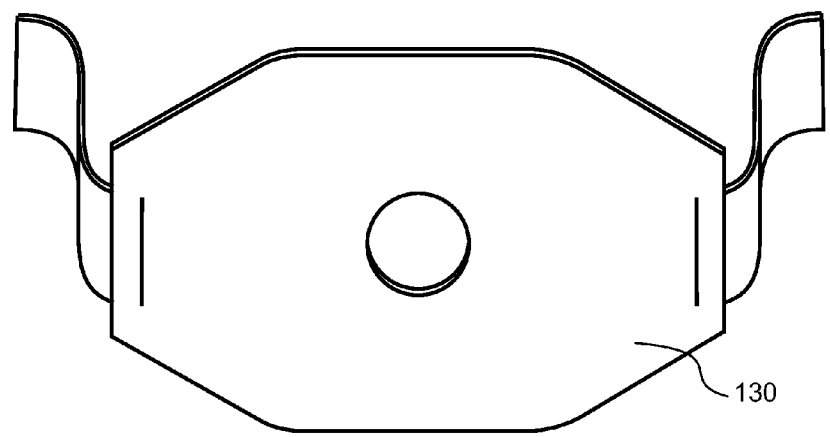
FIG. 13 shows a trachea interface (mask).
Figure 14:
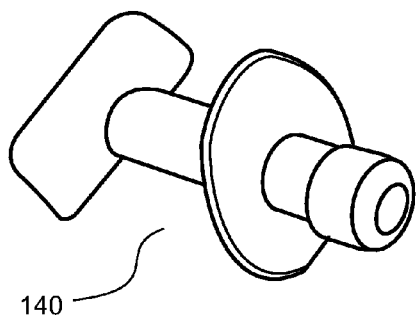
FIG. 14 shows a stoma (trachea) button.
Figure 15:
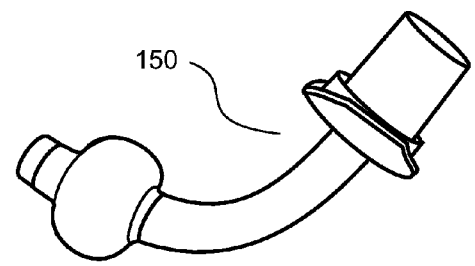
FIG. 15 shows a tracheostomy tube.
Figure 16:
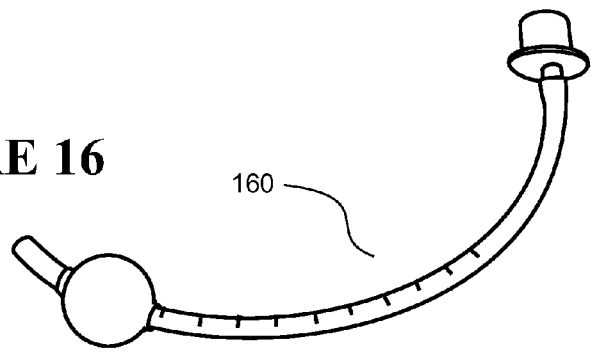
FIG. 16 shows an endotracheal tube.
Figure 17:
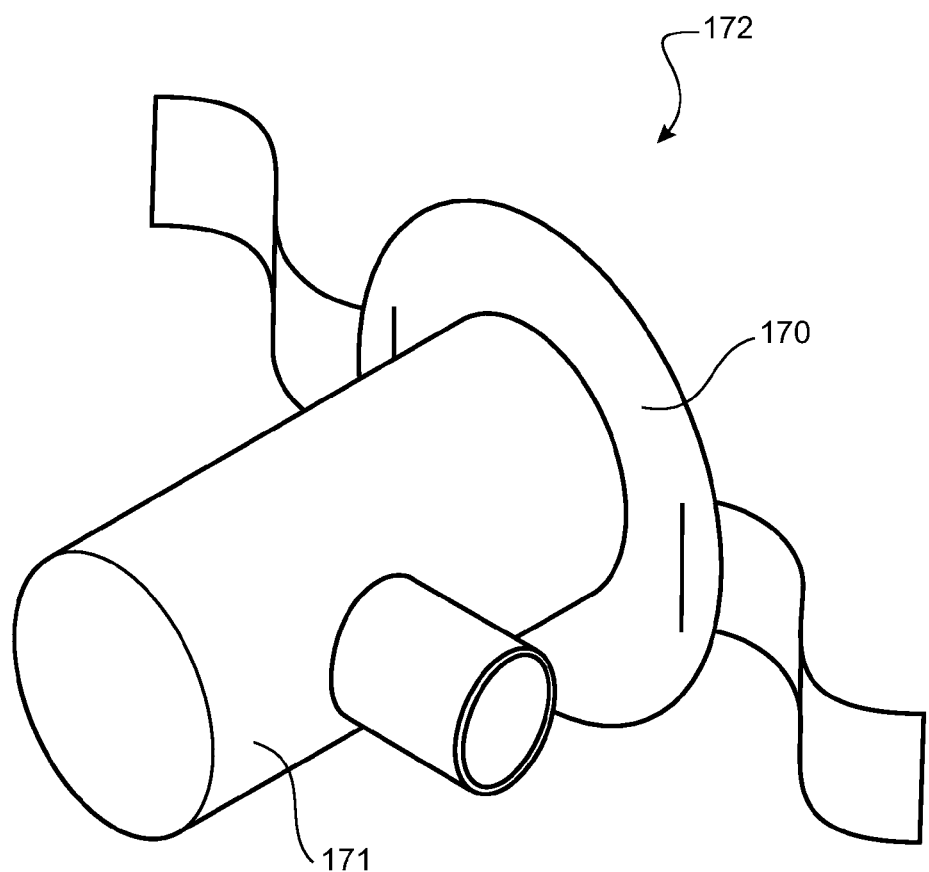
FIG. 17 shows a trachea interface comprising a body and mask.
Figure 23:
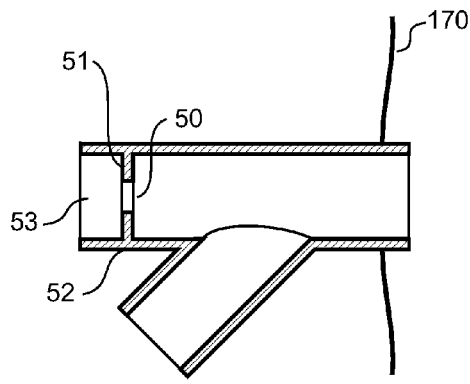
Figure 24:
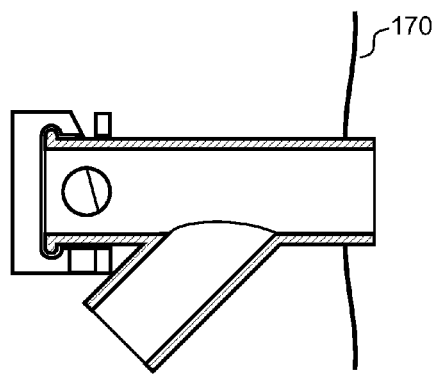
Figure 25:
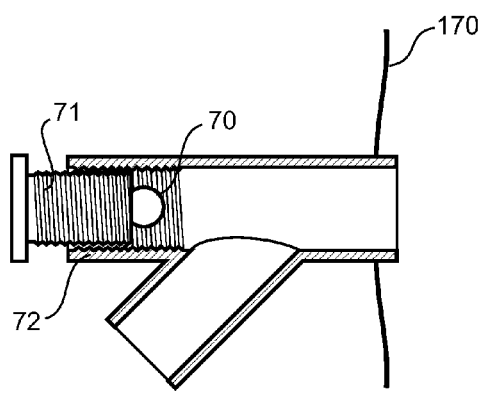
Figure 26:
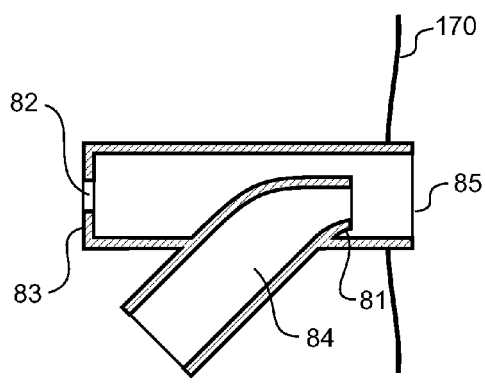
Figure 27:
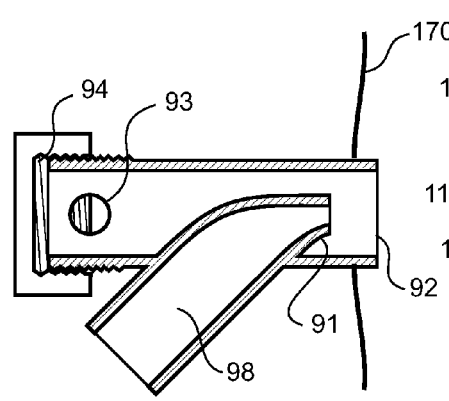
Figure 28:
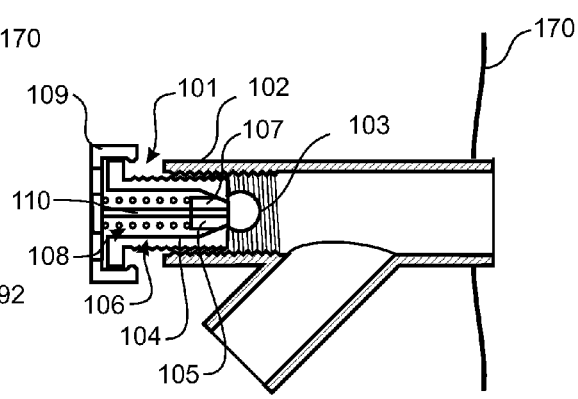

A prior art tracheal coupling (in the form of a connector) shown in FIGS. 2A and 2B provides an outlet port of about the same cross section as the inlet port and the patient port. In the high flow environment, the connector produces a very small pressure in the patient airway. Referring to FIG. 11, with a flow of 50 liters per minute, this connector produced a pressure as illustrated in section B of the pressure plot. In this section, maximum PEEP (Positive End Expiratory Pressure) was less than 1 cm $H_2O$.

The tracheal couplings according to the present invention include adaptations to work with the high flow environment (for example with the flow generator 13 in FIG. 1) to produce an elevated pressure in the patient airway and PEEP. Because a large portion of the supplied gases are exhausted direct to the room, there is a tolerance for variation in the delivered flow rate. The tracheal couplings of the present invention provide a level of pressure support that varies depending on the flow rate delivered to the connector. The clinician can use variation of the flow rate supplied to the tracheal coupling of the present invention to vary the pressure support for the patient. Exhaust gas flow rates may be regulated by fixing the restriction to gas flow through variable or non-variable adaptations. The end expiratory pressure experienced by a user can therefore be regulated. A positive end expiratory pressure (PEEP) can keep the airways and alveoli from collapsing at end-expiration and reopen airways and alveoli that have already collapsed. The therapeutic provision of PEEP can improve gas exchange (decreased intra pulmonary shunt), reduce the resistance to airflow (lung resistance), and makes the lungs less stiff (increased lung compliance). Levels of oxygen and carbon dioxide also may improve, reducing the need for supplemental oxygen and the sensation of breathlessness. PEEP may also improve cardiac performance by increasing mean intra thoracic pressure. PEEP is of special advantage to assisting in the treatment of obstructive lung diseases and heart, failure, including emphysema, bronchiectasis, chronic bronchitis, cystic fibrosis and pulmonary edema.

A number of variations of tracheal couplings according to the present invention are illustrated in FIGS. 3A to 10, 12 and 17 to 28 and described below. FIGS. 3A to 10, 12 show connectors, while FIGS. 17 to 28 show trachea interfaces. These tracheal couplings can provide for interfacing between a patient and gases supply. These tracheal couplings include a range of features for producing an elevated internal pressure from the flow flowing through the tracheal couplings in order to provide PEEP. The invention also contemplates tracheal couplings incorporating more than one of these adaptations. Examples of tracheal couplings incorporating multiple adaptations are illustrated in FIGS. 6, 8 and 9 and FIGS. 24, 26 and 27. Nonetheless, other combinations of these features are also possible and within the scope of the invention.

Figure 3A:
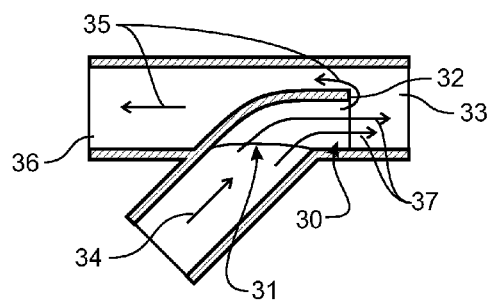
FIGS. 3A and 3B are cross sectional views of a trachea connector according to one aspect of the present invention.
Figure 3B:
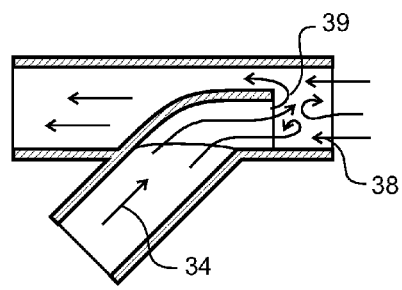

FIGS. 3A and 3B illustrate a tracheal coupling in the form of a connector including a directed flow nozzle 30 extending from the inlet port 31. The directed flow nozzle 30 includes an outlet end 32 facing towards the patient port 33. The outlet end 32 of the nozzle 30 is smaller than the inlet port area and the inlet flow 34 accelerates through the nozzle 30. During inhalation, a portion 35 of the flow 34 flows directly to the outlet port 36. The remainder 37 flows through the patient port 33 to be inhaled by the patient. As can be seen in FIG. 3B, when the patient exhales, the flow of exhaled gases 38 is opposed by the incoming gases 39. The opposed flows create a zone of turbulence adjacent the nozzle outlet 32. This turbulent flow zone resists with the patient exhalation flow 38 to create an elevated pressure at the patient port of the connector.

The flow nozzle could extend beyond patient port into tracheostomy tube or other trachea insert/interface the connector is used with. This could include a bend so that the nozzle turns the inlet flow into line with the patient airway. The nozzle would not extend further than necessary to make this turn For example, the portion in line with the patient airway would be no more than 30 mm long. So it would not irritate mucosa in the trachea.

Figure 4A:
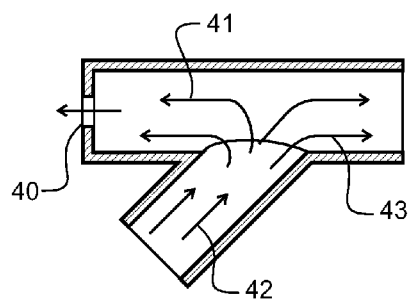
FIGS. 4A and 4B are cross sectional side elevations of a trachea connector according to a second aspect of the present invention.
Figure 4B:
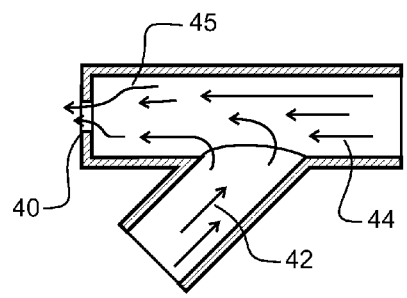

FIGS. 4A and 4B illustrate another connector including a flow restriction at the outlet end. The flow restrictor may be in the form of a wall partially closing the end of the connector. The wall includes an aperture 40 of a particular size, the area of the aperture 40 being smaller than the cross sectional area of the inlet port. Flow from the outlet end of the connector is restricted by the port 40, producing a back pressure in the connector that is a function of the flow rate through the aperture.

As illustrated in FIG. 4A, during inhalation, a portion 41 of the incoming flow 42 flows directly to the aperture 40, while a portion 43 is inhaled by the patient. As illustrated in FIG. 4B, during patient exhalation, all of the incoming air 42 and the exhaled air 44 combines, and the combined flow 45 flows through aperture 40.

This greater combined flow during exhalation leads to a greater pressure within the connector during patient exhalation. The aperture may be substituted by multiple apertures, or a screen, mesh or filter.

In practice, a range of connectors may be provided with apertures 40 of different size (cross sectional area). A clinician may select a connector from this range according to the flow and pressure support needs of their patient. For example, a connector with a certain aperture size may be rated to provide a first pressure support with a first flow level, a second (greater) pressure support at a second (greater) flow level, a third (still greater) pressure support at a third (still greater) flow level and so on. Another connector with a larger aperture may be rated to provide the first pressure support at the second flow level. Another connector with a smaller aperture may be rated to provide the second pressure support at the first flow level. The clinician, knowing the pressure support desired and the flow rated intended to be used, can select the connector with the closest matching pairing of flow and pressure. This selection could be facilitated by a chart of pressure support against flow, with each connector being represented in the chart in the form of a region or band. The clinician would select pressure support on one scale and flow on the other scale. The point on the chart indicated by these selections would fall in the region or band of a connector suitable for supplying that combination of flow and pressure support.

Figure 5:
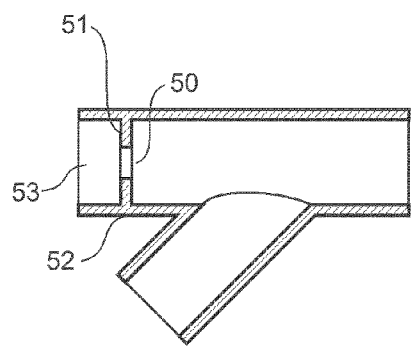
FIG. 5 is a cross sectional side elevation of a trachea connector according to a further aspect of the present invention where a restriction is provided intermediately located between the inlet port and the outlet port.

FIG. 5 illustrates a variation of the connector of FIGS. 4A and 4B, including a fixed flow restricting aperture 50 at a location intermediate between the inlet port and the outlet port. This aperture 50 may be provided in a wall 51 within the connector. Alternatively the intermediate restriction could be provided by a neck in the surrounding wall 52 of the connector. The subsequent expanded portion 53 of the outlet may allow other components with a male connector to be fitted to the tracheal connector, with the portion 53 acting as a female interface.

Figure 6:
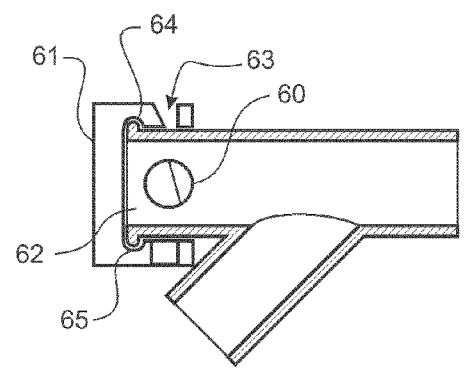
FIG. 6 is a cross sectional side elevation of a trachea connector according to a further aspect of the present invention including an adjustable flow restriction.

FIG. 6 illustrates a connector including an adjustable outlet aperture. The adjustable outlet aperture includes a primary aperture 60 in the wall of the connector. A cap 61 covers the outlet end 62 of the connector. The cap 61 includes a tapered slot 63 at generally the same longitudinal location as the aperture 60 when the cap 61 is fitted to the connector. Rotation of the cap 61 changes the part of slot 63 which intersects with aperture 60. More of less of the aperture 60 can be exposed to the internal portion of the connected, by rotation of the cap 61 to adjust the amount of intersection of the slot 63 and the aperture 60. Multiple apertures 60 may be provided on the outlet portion 62 of the connector and multiple slots on the cap 61.

Preferably the slot and aperture or slots and apertures are configured so that for all positions of the cap there will be some outlet aperture exposed at all times, namely at least some intersection of the slot 63 and the aperture 60 always exists.

The cap 61 may be retained on the end of the tracheal connector by any suitable arrangement. In the illustrated arrangement, an outwardly extending lip 64 at the end of the connector engages in an inwardly extending channel of the cap 61. The cap 61 might be moulded, for example, from a plastics material, or from an elastomeric material such as silicone. An elastomeric material which would allow for internal undercuts to be moulded more easily. An elastomeric material would also provide a frictional engagement on the connector to maintain the rotational position of the cap.

Figure 7:
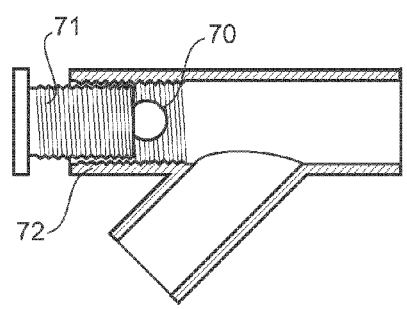
FIG. 7 is a cross sectional side elevation of a trachea connector according to a further aspect of the present invention including an alternative adjustable restriction.

FIG. 7 illustrates an alternative connector including an adjustable aperture. In this version, one or more primary apertures 70 are provided in the wall of the connector. A plug 71 may be adjusted into and out of the outlet end. An end portion of the plug partially overlaps the outlet apertures 70 by a degree that varies according to the longitudinal position of the plug.

In the illustrated arrangement the plug includes an external thread which engages with an internal thread in the outlet end 72 of the connectors for adjusting the longitudinal position of plug 71. Rotation of the plug in a first direction draws the plug into the connector. Rotation of the plug in a second direction (relative to the connector) progressively withdraws the plug from the connector to progressively open the outlet aperture.

Numerous alternative arrangements for providing an adjustable outlet aperture may suggest themselves and be within the scope of the present invention. Many arrangements for providing a minimum flow aperture may also suggest themselves, for example, movement of any adjusting member (such as plug 71 of cap 61) may be limited so that at all times at least part of the primary outlet aperture remains uncovered. Alternatively one or more additional by-pass outlets may be provided through the body of the connector, or through any adjusting member (such as through the end of cap 61 or through the body of plug 71).

The cap 61 of the embodiment of FIG. 6 may be reconfigured to be a hollow plug on the inside of the connector. Similarly, the plug 71 of the embodiment of FIG. 7 may be reconfigured to be a cap with a wall around the outside of the connector. This could for example have a threaded wall like that shown in FIG. 9, or a frictional engagement portion like that shown in FIG. 6. Other arrangements for opening and closing a flow passage by adjusting the position of a covering or closing member may also be used, such as a ball cock or similar valve.

Figure 8:
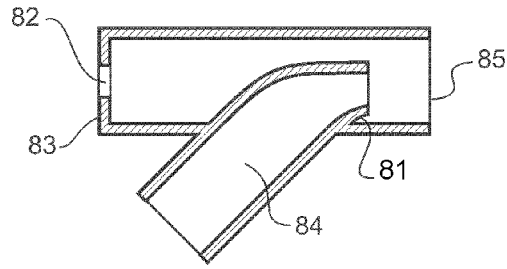
FIG. 8 is a cross sectional side elevation of a trachea connector according to a further aspect of the present invention incorporating flow restrictions in the form of a restricted outlet and a jet-generating nozzle.

FIG. 8 illustrates a connector including a turbulent flow generator and an outlet restriction. The turbulent flow generator comprises nozzle 81 extending from the inlet port 84 and directed toward the patient port 85. The outlet flow restriction comprises an aperture 82 in end wall 83 closing the outlet end of the connector. Of course, other forms of adjustable flow restriction may be provided and other forms of turbulent flow generating nozzle. According to one example the nozzle may be configured to deliver a swirling or vortex flow into the tracheostomy or ET tube or other trachea insert/interface that the connector is connected to. This might have some benefit in clearing the airway of the tube.

Figure 9:
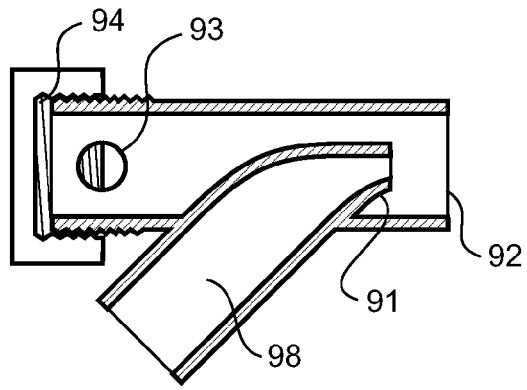
FIG. 9 is a cross sectional side elevation of a trachea connector according to a further aspect of the present invention illustrating the combination of a turbulence-generating nozzle and a variable restricted outlet.

FIG. 9 illustrates an arrangement including a turbulence generator and a flow restriction. In this case, the connector includes a turbulence generating nozzle 91 extending from the inlet port 98 toward the patient port 92. At the outlet end, the connector includes an adjustable flow restriction in a form similar to the flow restriction of FIG. 7. The adjustable flow restriction includes a primary aperture 93 and a cap 94 which fits over the outlet end of the tracheal connector. The cap 94 is threaded over the end of the tracheal connector and can be advanced or retreated along the body of the connector by rotating the cap relative to the connector. Accordingly, the degree to which the cap 94 covers the primary apertures 93 can be adjusted.

Figure 10:
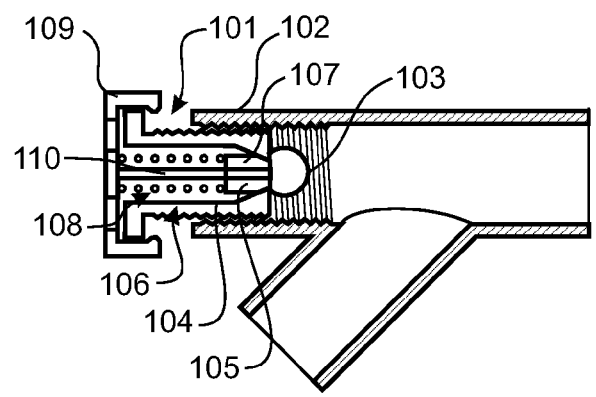
FIG. 10 is a cross sectional side elevation of a trachea connector according to a further aspect of the present invention including an adjustable restricted outlet and a pressure relief valve.

FIG. 10 illustrates a further embodiment of the tracheal connector. This embodiment includes a variable flow restriction of the type shown in FIG. 7 with a plug 101 fitted in the outlet end 102 of the tracheal connector. The plug covers a plurality of openings/outlet apertures 103 to a degree that depends on how far the plug 101 is threaded into the body of the connector.

In the embodiment of FIG. 10, the plug 101 includes a pressure relief valve, the pressure relief valve maybe in any suitable form, and could alternatively be provided through the body of the connector in any suitable location along the wall of the connector. The valve could be passively activated or actively controlled, for example, by a solenoid energisable by the flow generator or monitoring system.

In the embodiment illustrated the pressure relief valve includes a passage way 104 through the body of the plug 101. A valve member 105 is seated against a tapered surface 107 at the tracheal connector end of the passage 104. The valve member 105 is held against the seat 107 by precompression of a coil spring 108. The coil spring is held in its compressed state by a cap 109 clipped onto the body of pipe 101. The valve member 105 may slide along a guide member 110 extending from the cover 109. The amount of pre-compression of spring 108 controls the relief pressure at which the valve member 105 withdraws from valve seat 107.

Any other known form of pressure relief valve may be incorporated as an alternative.

Each connector shown in FIGS. 3A to 10 could be adapted for interfacing with a patient by connection to any type of trachea insert/interface, such as an endotracheal tube, tracheostomy tube, stoma (trachea) button, laryngeal mask or the like. FIGS. 13 to 16 show examples of each, which are know in the art. A trachea interface 130 is a removable interface that can be attached to the neck of a patient with a tube for insertion into the trachea, such as that shown in FIG. 13. A stoma button 140 is permanently inserted into the trachea of a patient, such as that shown in FIG. 14. Tracheostomy tubes 150 and endotracheal tubes 160 are inserted further into the trachea, such as that shown in FIGS. 15 and 16 respectively. The patient end of a connector can be coupled to a trachea insert/interface in any suitable manner, for example by a friction push fit. The term "trachea insert" or "trachea interface" can be used interchangeably to more generally refer to any of the abovementioned or other related apparatus.

FIG. 11 illustrates supporting pressure that can be generated using the illustrated tracheal connectors in a high flow supply environment. FIG. 11 plots internal pressure at the open end of the tracheostomy tube against time to show how the pressure varies during a patient breathing cycle. These plots were generated using sample connectors connected to a lung simulator. The sample connector is supplied with inlet gases at the inlet port, from a gas supply set to deliver 50 liters per minute.

Portion A of the trace of FIG. 11 was generated by the prior art connector similar to FIGS. 2A and 2B when supplied without flow. The negative pressures are the result of suction from the simulated inhalations.

Portion B of the trace in FIG. 11 was generated using the prior art connector with a flow of 50 liters per minute. It can be seen from this trace that the average pressure support is approximately 0.5 cm $H_2O$ and the maximum expiratory back pressure is approximately 0.75 cm $H_2O$.

Portion C of the trace in FIG. 11 was generated using a connector having a flow restricting orifice of a first size. In this connector, the flow restricting orifice was 79 $mm^2$ cross section area, with the body of the connector having an internal cross section of 165 $mm^2$. This connector produced a peak pressure support (PEEP) of approximately 2 cm $H_2O$.

Portion D of the trace in FIG. 11 was generated using a connector having a flow restricting orifice of a second size. At this connector, the flow restricting orifice was 24 $mm^2$ cross section area, with the body of the connector having a cross section of 165 $mm^2$. This connector produced a peak pressure support (PEEP) of approximately 11 cm $H_2O$.

The general form of a trachea connector according to the present invention is described above. Within that general form wide variations are possible but certain particulars are preferred.

The trachea connector preferably includes a socket at the patient port to connect with a male 15 mm medical connector typical of standard tracheostomy and ET tubes. Tracheostomy tubes conforming to ISO standard 5366-1:2000 should have a permanently attached male 15 mm conical connector in accordance with ISO 5356-1.

The connector should be relatively small, for example with an overall length of inlet tube of approximately 20 mm and overall length of main tube of approximately 40 mm. A range of length of inlet tube of 210 mm to 50 mm is contemplated. A range of length of main tube of 30 mm to 80 mm is possible with the lower end of this range preferred. The inner diameter of the main tube may be about 15 mm. The inner diameter of the inlet tube may be about 10 mm.

The inlet tube preferably intercepts with the main tube at an angle that forms in an obtuse angle with the patient port and an acute angle with the outlet port. An angle of about 60 degrees between the main tube and the inlet tube may be appropriate.

Figure 12:
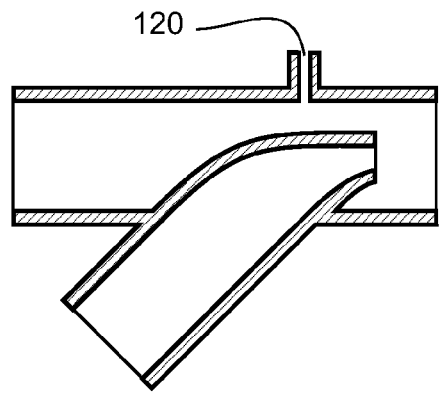
FIG. 12 is a cross sectional side elevation of a trachea connector according to a further aspect of the present invention illustrating the combination of a turbulence-generating nozzle and a sensor port.

As shown in FIG. 12, one or more additional ports 120 may be included on the connector for use with sensors for monitoring properties of the gas. For example, potential sensors that could be usefully integrated with the connector include a pressure sensor or a $CO_2$ sensor. In a medical environment a standard luer port formed in a sidewall of the connector would be appropriate. A port for a $CO_2$ sensor or pressure sensor could be included anywhere along the wall of the main tube. The port 120 in FIG. 12 is shown on the embodiment of FIG. 3A by way of example. It could apply to any of the other embodiments in FIGS. 3B to 10, 12 and 17 to 28.

The connector may be made from any suitable medical plastic or polymer. The plastic may be substantially rigid (by its material and detailed shape) so that it does not deform significantly under the fluctuating pressure support generated by patient breathing.

The above describes preferred forms of the trachea connector according to the present invention. Widely differing embodiments will suggest themselves to a person skilled in the art without departing from the scope of the invention as to finding appended claims.

The tracheal coupling could also take the form of a trachea interface 172 that can be attached directly to a tracheotomised patient. Such a coupling is shown generally in FIG. 17. The trachea coupling comprises an interface 170 such as that shown in FIG. 17 integrated with a body portion 171 such as any of those connector embodiments shown in FIGS. 3A to 10. The tracheal coupling in the form of a trachea interface 172 might further comprise an additional tube/coupling connected to that patient end that inserts into the trachea of a patient. Alternatively, the patient end of the trachea interface might insert directly into the trachea.

Examples embodiments of tracheal couplings in the form of a trachea interface 172 are shown in FIGS. 18 to 28. The body portion any of those embodiments could take the form of any of the connectors shown in FIGS. 3A to 10, 12. The description for FIGS. 3A to 10, 12 applies to the body portion of the trachea interfaces shown in FIGS. 17 to 28.

As shown in FIG. 2, one or more additional ports 120 may be included on the trachea interface for use with sensors for monitoring properties of the gas. For example, potential sensors that could be usefully integrated with the connector include a pressure sensor or a $CO_2$ sensor. In a medical environment a standard leer port formed in a sidewall of the connector would be appropriate. A port for a $CO_2$ sensor or pressure sensor could be included anywhere along the wall of the main tube. The port 120 in FIG. 22 is shown on the embodiment 18 by way of example. It could applied to any of the other embodiments in FIGS. 17 to 28.

The trachea interface may be made from any suitable medical plastic or polymer. The plastic may be substantially rigid (by its material and detailed shape) so that it does not deform significantly under the fluctuating pressure support generated by patient breathing.

All the trachea couplings described herein can be used in conjunction with the blower 13 and conduit 10 system shown in FIG. 1

The above describes preferred forms of the trachea connector according to the present invention. Widely differing embodiments will suggest themselves to a person skilled in the art without departing from the scope of the invention as to finding appended claims.

The invention claimed is:

1. A tracheal coupling for interfacing between a patient and a gases source, the coupling comprising:
a patient port for connecting to a trachea interface in or on a patient;
an outlet end;
a wall extending between the patient port and the outlet end;
an inlet port for receiving an incoming flow of gases from the gases source, the inlet port defining an outflow end, wherein an entirety of the outlet end is spaced from the outflow end along an axis of the wall and is located on an opposite side of the outflow end from the patient port; and
a flow restriction to restrict expiratory flow in use to produce PEEP of at least 1 cm $H_2O$ when flow to the inlet port is 50 liters per minute, the flow restriction located between the outflow end and the outlet end or at the outlet end, the flow restriction comprising an aperture having an area smaller than a cross-sectional area of the outflow end of the inlet port, the flow restriction comprising a blocking element configured to block a portion of the aperture, wherein the blocking element is adjustable to allow adjustment of the portion of the aperture blocked by the blocking element.

2. The tracheal coupling as claimed in claim 1, in combination with a humidification chamber.

3. The tracheal coupling as claimed in claim 1, further comprising a pressure relief valve.

4. The tracheal coupling as claimed in claim 1 in combination with the trachea interface, wherein the trachea interface comprises one or more of:
a trachea button,
an endotracheal tube,
a tracheostomy tube,
a laryngeal mask.

5. A system for supplying breathing gases to a patient, the system comprising an airflow source including an adjustable flow control, and the tracheal coupling according to claim 1, wherein the PEEP produced by the coupling can be set by the adjustable flow control of the airflow source.

6. The tracheal coupling as claimed in claim 1, wherein the outlet end is defined by or within a boundary of the wall.

7. The tracheal coupling as claimed in claim 1, wherein the blocking element blocks the aperture from an interior of the wall.

8. The tracheal coupling as claimed in claim 1, wherein the blocking element blocks the aperture from an exterior of the wall.

9. The tracheal coupling as claimed in claim 1, wherein, during inhalation by the patient, a first portion of the incoming flow flows directly through the aperture and a second portion of the incoming flow flows through the patient port to be inhaled by the patient, and during exhalation by the patient, all of the incoming flow and the expiratory flow combines and the combined flow flows through the aperture.

10. The tracheal coupling as claimed in claim 1, wherein a jet flow from the inlet port resists the combined flow flowing to the outlet end.

11. The tracheal coupling as claimed in claim 1, wherein the inlet port is defined by a second wall, at least a portion of the second wall being disposed outside of the wall extending between the patient port and the outlet end.

12. The tracheal coupling as claimed in claim 11, wherein a part of the second wall is disposed closer to the outlet end than is the outflow end of the inlet port.

13. The tracheal coupling as claimed in claim 1, wherein the inlet port further comprises an inlet axis that intersects the axis of the wall.

14. The tracheal coupling as claimed in claim 13, wherein the inlet axis forms an acute angle with a portion of the axis of the wall that extends between the outlet end and the inlet port.

15. The tracheal coupling as claimed in claim 1, wherein an entirety of gas passing through the patient port and toward the trachea interface is provided by the incoming flow of gases passing through the inlet port.

16. A method of providing breathing gases to a patient comprising:
   a) attaching the tracheal coupling to a breathing tube of the patient, the tracheal coupling comprising a patient port connected to a trachea interface in or on a patient, an outlet end, a wall extending between the patient port and the outlet end, an inlet port for receiving an incoming flow of gases from a gases source, the inlet port defining an outflow end, wherein an entirety of the outlet end is spaced from the outflow end along an axis of the wall and is located on an opposite side of the outflow end from the patient port and a flow restriction to restrict expiratory flow in use to produce PEEP of at least 1 cm $H_2O$ when flow to the inlet port is 50 liters per minute, the flow restriction located between the outflow end and the outlet end or at the outlet end, the flow restriction comprising an aperture having an area smaller than a cross-sectional area of the outflow end of the inlet port, the flow restriction comprising a blocking element configured to block a portion of the aperture, wherein the blocking element is adjustable to allow adjustment of the portion of the aperture blocked by the blocking element;
   b) selecting a flow level for a supply of gases to the coupling to generate a desired amount of PEEP;
   c) supplying the flow level of gases to the inlet port of the coupling.

17. The method of claim 16, wherein during inhalation by the patient, a first portion of the incoming flow flows directly through the aperture and a second portion of the incoming flow flows through the patient port to be inhaled by the patient, and during exhalation by the patient, all of the incoming flow and the expiratory flow combines and the combined flow flows through the aperture.

18. A method of providing breathing gases to a patient comprising:
   a) attaching the tracheal coupling to a breathing tube of the patient, the tracheal coupling comprising a patient port connected to a trachea interface in or on a patient, an outlet end, a wall extending between the patient port and the outlet end, an inlet port for receiving an incoming flow of gases from a gases source, the inlet port defining an outflow end, wherein an entirety of the outlet end is spaced from the outflow end along an axis of the wall and is located on an opposite side of the outflow end from the patient port and a flow restriction to restrict expiratory flow in use to produce PEEP of at least 1 cm $H_2O$ when flow to the inlet port is 50 liters per minute, the flow restriction located between the outflow end and the outlet end or at the outlet end, the flow restriction comprising an aperture having an area smaller than a cross-sectional area of the outflow end of the inlet port, the flow restriction comprising a blocking element configured to block a portion of the aperture, wherein the blocking element is adjustable to allow adjustment of the portion of the aperture blocked by the blocking element;
   b) adjusting the blocking element for the coupling according to an expected flow of gases and a desired amount of PEEP,
   c) supplying a flow of gases to the inlet port of the coupling.

19. The method of claim 18, wherein, during inhalation by the patient, a first portion of the incoming flow flows directly through the aperture and a second portion of the incoming flow flows through the patient port to be inhaled by the patient, and during exhalation by the patient, all of the incoming flow and the expiratory flow combines and the combined flow flows through the aperture.

* * * * *